US008505236B1

(12) United States Patent
Morales-Ramos et al.

(10) Patent No.: US 8,505,236 B1
(45) Date of Patent: Aug. 13, 2013

(54) APPARATUS FOR PACKAGING ARTHROPODS INFECTED WITH ENTOMOPATHOGENIC NEMATODES

(75) Inventors: Juan A. Morales-Ramos, Greenville, MS (US); W. Louis Tedders, Perry, GA (US); Carl Brian Dean, Leland, MS (US); David I. Shapiro-Ilan, Macon, GA (US); Maria Guadalupe Rojas, Greenville, MS (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 287 days.

(21) Appl. No.: 12/953,719

(22) Filed: Nov. 24, 2010

Related U.S. Application Data

(60) Provisional application No. 61/265,098, filed on Nov. 30, 2009.

(51) Int. Cl.
*A01M 1/20* (2006.01)
(52) U.S. Cl.
USPC ............................................ 43/132.1; 43/131
(58) Field of Classification Search
USPC .................................. 43/107, 121, 131, 132.1
See application file for complete search history.

(56) References Cited

U.S. PATENT DOCUMENTS

| 2,160,367 | A | * | 5/1939 | Maxfield ........................ 53/433 |
| 3,785,556 | A | * | 1/1974 | Watkins ........................... 239/6 |
| 3,874,146 | A | * | 4/1975 | Watkins ......................... 53/554 |
| 4,859,377 | A | * | 8/1989 | Shasha et al. .................. 264/4.1 |
| 5,085,036 | A | * | 2/1992 | Evans et al. ..................... 53/550 |
| 5,358,863 | A | * | 10/1994 | Quimby et al. ............... 435/178 |
| 5,997,945 | A | * | 12/1999 | Shasha et al. .............. 427/213.3 |
| 6,057,145 | A | * | 5/2000 | Ishibashi ....................... 435/243 |
| 6,184,434 | B1 | * | 2/2001 | Raulston et al. .................. 800/8 |
| 6,524,601 | B1 | * | 2/2003 | Shapiro et al. ................ 424/405 |
| 7,374,773 | B1 | * | 5/2008 | Shapiro-Ilan et al. ........ 424/406 |
| 2004/0251164 | A1 | * | 12/2004 | Yasuike et al. ............. 206/524.4 |
| 2008/0295774 | A1 | * | 12/2008 | Van Beek et al. ............. 119/6.6 |
| 2009/0044495 | A1 | * | 2/2009 | Aylward ........................ 53/473 |

FOREIGN PATENT DOCUMENTS

BR  8701832  *  4/2009

* cited by examiner

*Primary Examiner* — David Parsley
(74) *Attorney, Agent, or Firm* — John Fado; Albert Y. Tsui; Lesley Shaw

(57) ABSTRACT

Disclosed is a taping apparatus for packaging arthropods having been infected with entomopathogenic nematodes wherein the tape forms a continuous line of packaged arthropods. In one embodiment of the invention, the tape formulation has the arthropods *Tenebrio molitor, Aethina tumida*, or *Diaprepes abbreviatus* infected with the nematodes of *Heterorhabditis indica* or *Steinernema carpocapsae*.

5 Claims, 12 Drawing Sheets

APPARATUS FOR PACKAGING ARTHROPODS INFECTED WITH ENTOMOPATHOGENIC NEMATODES

CROSS-REFERENCE TO RELATED APPLICATION

Figure 1:
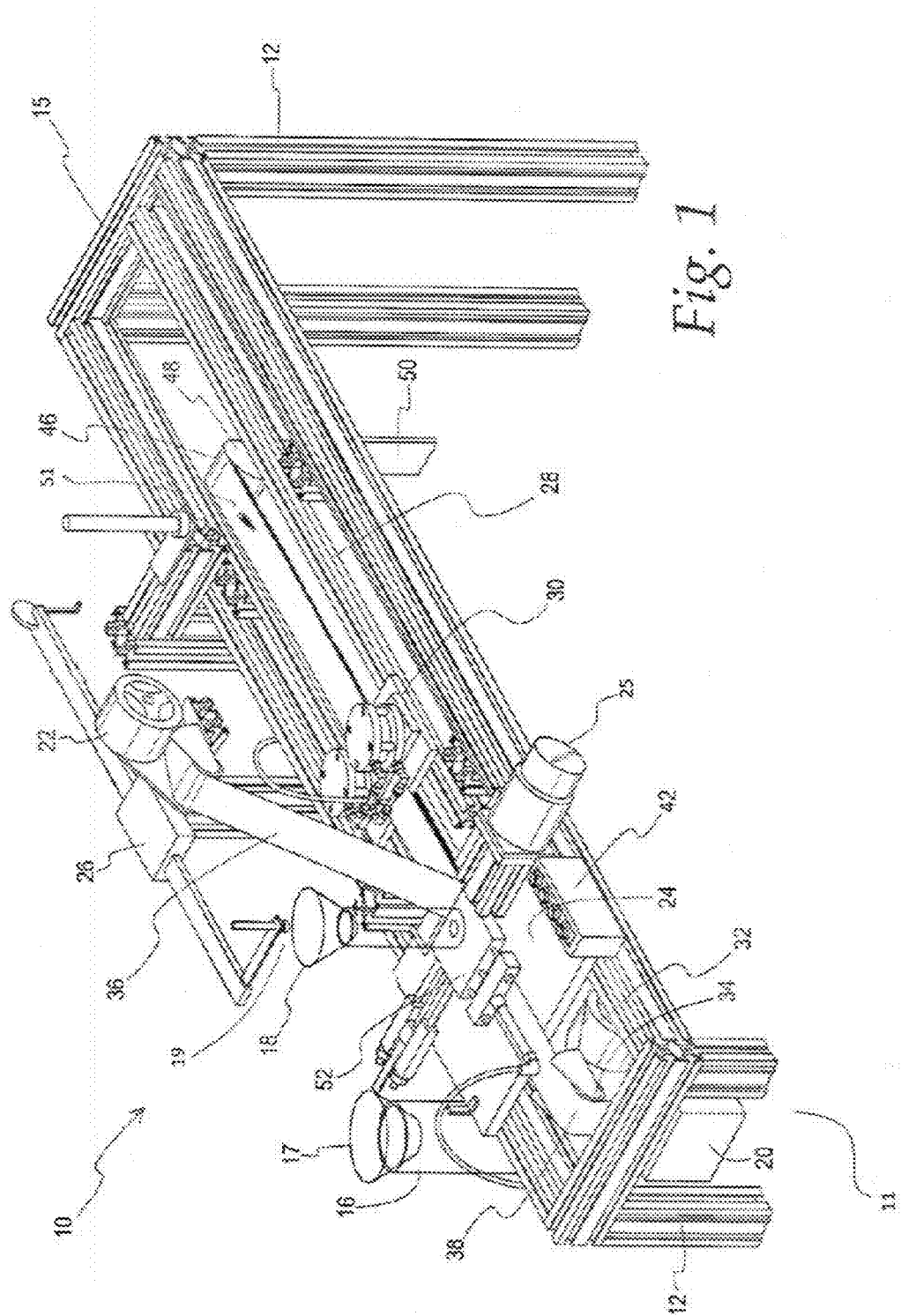

This present application claims priority under 35 U.S.C. §119(e) to U.S. Provisional Ser. No. 61/265,098, which was filed on Nov. 30, 2009, the application is hereby incorporated by reference.

FIELD OF THE INVENTION

This invention relates to the field of agriculture and biological control of pests. In particular, the invention provides of a packaging apparatus for taping arthropods infected with entomopathogenic nematodes by flanking the infected arthropods between two pieces of pressure sensitive tape. Also the invention provides for methods for pest control by use of infected arthropods flanked between two pieces of pressure sensitive tape.

BACKGROUND OF INVENTION

Entomopathogenic nematodes are important biological control agents for a variety of economically important pests in agricultural and urban environments (Grewal and Georgis, Entomophathogenic nematodes, "Methods in Biotechnology", Volume 5, Biopesticides: Use and Delivery, F. R. Hall and J. J. Menn, Eds., 271-299, 1998, Totowa, N.J., Humana Press, Inc.; Kaya and Gaugler, Entomopathogenic Nematodes, Annu Rev. Entomol., Volume 38, 181-206, 1993). Specific entomopathogenic nematodes, *Steinernema* and *Heterorhabditis*, are important biological control agents for a variety of economically important pests. The nematodes can be mass-produced using in vivo or in vitro methods (Shapiro-Ilan, D. I., Gaugler, R., 2002. Production technology for entomopathogenic nematodes and their bacterial symbionts. J. Ind. Microbiol. & Biotech. 28, 137-146; Ehlers, R-U., Shapiro-Ilan, D. I., 2005. Mass production. In: Grewal, P. S., Ehlers, R-U, Shapiro-Ilan, D. I. (Eds.), Nematodes as Biocontrol Agents. CABI Publishing, Wallingford, UK, pp. 65-78). Additionally, U.S. Pat. No. 6,474,259 discloses in vivo, apparatus and methods for producing insecticidal nematodes resulting in the nematodes harvested into an aqueous solution.

Current commercial entomopathogenic nematodes are generally applied as infective juveniles (Us) in aqueous suspensions using various irrigation systems, sprayers, or injection techniques (Grewal, P. S., 2002. Formulation and application technology. In: Gaugler, R. (Ed.), Entomopathogenic Nematology. CABI Publishing, Wallingford, UK, pp. 265-288; Creighton, C. S., Fassuliotis, G., 1985. *Heterorhabditis* sp. (Nematoda: Heterorhabditidae): A nematode parasite isolated from the banded cucumber beetle *Diabrotica balteata*. J. Nematol. 17, 150-153).

Entomopathogenic nematodes may also be applied in infected insect arthropods (Creighton, C. S., Fassuliotis, G., 1985. *Heterorhabditis* sp. (Nematoda: Heterorhabditidae): A nematode parasite isolated from the banded cucumber beetle *Diabrotica balteata*. J. Nematol. 17, 150-153; Jansson, R. K., Lecrone, S. H, Gaugler, R., 1993. Field efficacy and persistence of entomopathogenic nematodes (Rhabditida: Steinernematidae, Heterorhabditidae) for control of sweetpotato weevil (Coleoptera: Apionidae) in southern Florida. J. Econ. Entomol. 86, 1055-1063; Shapiro-Ilan, D. I., Lewis, E. E., Tedders, W. L., Son, Y., 2003. Superior efficacy observed in entomopathogenic nematodes applied in infected-host arthropods compared with application in aqueous suspension. J. Invertebr. Pathol. 83, 270-272; Bruck, D. J., Shapiro-Ilan, D. I., Lewis, E. E., 2005. Evaluation of application technologies of entomopathogenic nematodes for control of the black vine weevil, *Otiorhynchus sulcatus*. J. Econ. Entomol. 98, 1884-1889; Del Valle, E. E., Dolinksi, C., Barreto, E. L. S., Souza, R. M., Samuels, R. I., 2008. Efficacy of *Heterorhabditis baujardi* LP77 (Nematoda: Rhabditida) applied in *Galleria mellonella* (Lepidoptera: Pyralidae) insect arthropods to *Conotrachelus psidii* (Coleoptera: Curculionidae) larvae. Biocontrol Sci. Technol. 18, 33-41). In this approach, nematode-infected arthropods are disseminated and pest suppression is subsequently achieved by the progeny infective juveniles that exit the arthropods. Laboratory studies indicate that nematode application in infected hosts may be superior to application in aqueous suspension (Shapiro, D. I., Glazer, I., 1996. Comparison of entomopathogenic nematode dispersal from infected hosts versus aqueous suspension. Environ. Entomol. 25, 1455-1461; Shapiro, D. I., Lewis, E. E., 1999. Comparison of entomopathogenic nematode infectivity from infected hosts versus aqueous suspension. Environ. Entomol. 28, 907-911; Perez, E. E., Lewis, E. E., Shapiro-Ilan, D. I., 2003. Impact of host arthropod on survival and infectivity of entomopathogenic nematodes (Rhabditida: Steinernematidae and Heterorhabditidae) under desiccating conditions. J. Invertebr. Pathol. 82, 111-118). Additionally, pest control trials have indicated that arthropod application can be superior in efficacy to aqueous application (Shapiro-Ilan, D. I., Lewis, E. E., Tedders, W. L., Son, Y., 2003. Additionally, superior efficacy was observed in entomopathogenic nematodes applied in infected-host arthropods compared with application in aqueous suspension. J. Invertebr. Pathol. 83, 270-272).

While arthropod applications have been shown to be advantageous over aqueous applications, a potential problem with the arthropod applications is that infected hosts can rupture or stick together during transport or distribution (Shapiro-Ilan, D. I., Lewis, E. E. Behle, R. W., McGuire, M. R., 2001. Formulation of entomopathogenic nematode-infected-arthropods. J. Invertebr. Pathol. 78, 17-23). As disclosed in U.S. Pat. No. 6,524,601, the problem of rupturing arthropods can be ameliorated in soft bodied hosts such as the greater wax moth, *Galleria mellonella* (L.) (Lepidoptera: Pyralidae), by coating the arthropods with a powder such as clay. Similarly, arthropod coatings were developed for application of *Heterorhabditis baujardi* Phan et al. (Del Valle et al., 2009). Another approach is to use hard-bodied insects, such as the yellow mealworm, *Tenebrio molitor* L. (Coleoptera: Tenebrionidae), for which the harder cuticle can naturally resist rupture and prevent arthropods from sticking together. Yet, use of hard-bodied infected hosts may still result in some rupturing, and furthermore use of arthropods in certain markets, such as home gardens, may be limited due to an aversion of touching insects (Kellert, S. R., 1993. Values and perceptions of invertebrates. Conservation Biol. 7, 845-855). Thus, there is a need to develop a formulation that protects arthropods and allows ease of handing may be beneficial for hard and soft bodied hosts. Additionally, a formulation that is amenable to mass production and standardization will facilitate successful commercialization of utilizing nematodes as a biological control method.

Additionally there is a cost-benefit in applying nematode in infected arthropods as compared to aqueous nematode applications inasmuch as the former requires less steps in the process and is thus less costly (Shapiro-Ilan and Gauger, 2002, supra). Furthermore, it has been reported that entomopathogenic nematodes can survive dry conditions for extended periods if they remain inside a host arthropod. Commercialization of nematode-infected arthropods has been prevented due to problems in storage and application (Koppenhofer, A., "Nematodes", *Field Manual of Techniques in Invertebrate Pathology*, Chapter 4-5 pg. 283-301, 2000). Nematode-infected hosts stick together or rupture during transport and/or application, which results in reduced efficacy. As such there is a need for confer additional protection to infected hosts arthropods to minimize disruption during transport and application of the biological control.

BRIEF SUMMARY OF THE INVENTION

Disclosed is a taping apparatus for packaging arthropods, the apparatus comprising a receptacle for holding arthropods having been infected with entomopathogenic nematodes, a first tension adjustable tape head for dispensing a first tape, a transferring means for transferring at least one arthropod from the receptacle to a position on said first tape with the arthropod adhering to the first tape, a second tension adjustable tape head for dispensing a second tape with said second tape positioned to adhere to a section of said first tape upon said first tape receiving said arthropod with the second tape adhering to the arthropod and first tape, a rotating stationary arm that applies pressure to said second tape with said first tape section having an arthropod positioned thereupon; and a means for translocating a section of tape with first and second tape adhered together along a linear path to allow said first tape to receive a subsequent arthropod from said transferring means, wherein the adhered tape form a continuous line of packaged arthropods.

In one embodiment of the invention, the taping apparatus comprises a power source configured to provide electric current to the taping apparatus; and a programmable control unit configured to control the taping apparatus unit and/or the power source.

In another embodiment, the transferring means is a vacuuming means that provides vacuum pickup of an arthropod from the receptacle and dispenses said arthropod to an aperture on drop plate, with said drop plate being positionable to deposit a dispensed arthropod from the aperture to a section on the first tape.

In another embodiment, the taping apparatus further comprises an agitator that agitates arthropods held in the receptacle.

In another embodiment, the translocation means is a tape clamp positioned to clamp on to a portion of adhered first and second sections of tape not having any arthropods in between said portions with the clamp traversing a rodless cylinder to allow subsequent transferring of arthropods to a position on the first tape.

In yet another embodiment, disclosed is a method for pest management, the method comprising infecting arthropods with a plurality of infective juvenile nematodes, flanking infected arthropods between two pieces of tape to form a continuous tape, placing the tape or pieces of tape having the infected arthropods at a site where emerging nematodes provide biological control over another a pest specie. In one embodiment, the method the arthropods are *Tenebrio molitor*. In another embodiment of the invention, the *Tenebrio molitor* are infected with *Steinernema* and/or *Heterorhabditis* spp. In yet another embodiment of the invention, the pest species is *Diaprepes abbreviatus* or *Aethina tuminda.*

BRIEF DESCRIPTION OF THE DRAWING

The present invention together with the above and other objects and advantages may best be understood from the following detailed description of the embodiment of the invention illustrated in the drawings, wherein:

FIG. 1 is an isometric view of the arthropod tape packaging apparatus.

FIG. 2 is an isometric view of the apparatus with the arthropod positioning module in an extended position.

FIG. 3 is an isometric view of the apparatus with the arthropod positioning module in a retracted position.

FIG. 4. is an isometric view of the apparatus with the tape clamp.

FIG. 5. is a isometric view of the apparatus where the first and second positioned to receive an arthropod from the arthropod positioning module.

FIG. 6 is a graph of the mean percentage of ruptured *Tenebrio molitor* arthropods. The arthropods had been infected with *Heterorhabditis indica* and either formulated in tape or not; subsequently, the arthropods were subjected to manual shaking to determine resistance to rupturing. Different letters above bars indicate statistically significant differences within each sample date (SNK test, $\propto=0.05$).

FIG. 7 is a graph of the mean percentage survival of *Diaprepes abbreviatus* larvae 10 days and 15 days following application of *Heterorhabditis indica* infected arthropods in a laboratory setting. Two infected *Tenebrio molitor* were placed in pots with five *D. abbreviatus* larvae. Different letters above bars indicate statistically significant differences within each sample date (SNK test, $\propto=0.05$).

FIG. 8 is a graph of the mean percentage survival of *Diaprepes abbreviatus* larvae 10 days and 15 days following application of *Heterorhabditis indica* infected arthropods in a greenhouse setting. Two infected *Tenebrio molitor* were placed in pots with five *D. abbreviatus* larvae. Different letters above bars indicate statistically significant differences within each sample date (SNK test, $\propto=0.05$).

FIG. 9 is a graph of the mean percentage survival of *Aethina tumida* larvae 10 days and 15 days following application of *Heterorhabditis indica* infected arthropods in a laboratory setting. Two infected *Tenebrio molitor* were placed in soil cups with 10 *A. tumida* larvae. Different letters above bars indicate statistically significant differences within each sample date (SNK test, $\propto=0.05$).

FIG. 10 is a graph depicting the survival of *Aethina tumida* larvae 10 days following application of *Heterorhabditis indica* infected arthropods in field conditions. Infected *Tenebrio molitor* cadaver application using a tape formulation, a standard cadaver application without tape, and a control of water were applied in field conditions in Perry, Ga., USA. Different letters above bars indicated statistical significance ($P<0.05$).

FIG. 11 is a wiring diagram for the packaging apparatus.

FIG. 12 is a pneumatic diagram of the packaging apparatus.

DETAILED DESCRIPTION OF THE INVENTION

Definitions

As used in the specification and claims, the singular form "a", "an" and "the" include plural references unless the context clearly dictates otherwise. For example, an arthropod having been infected with a "nematode" includes plurality of nematodes.

The term "pressure sensitive tape" is a tape structure having pressure sensitive adhesive coated on at least on one side of the backing material. The adhesive is not heated or solvent activated and adheres upon application of light pressure.

The term "arthropod" refers to any invertebrate having an exoskeleton. In accordance with the arthropod taping apparatus disclosed herein, the type of arthropods to be used in a taped formulation is not limited to the arthropods provided in the Examples herein. Preferably, the arthropods to be taped has not molted its exoskeleton recently so as to confer facile handling and packing Preferably the arthropod has a hard exoskeleton that does not stick or rupture which includes but is not limited to insects in the family Tenebrionidae, e.g., *T. molitor*, *Zophobas morio*, and the lesser mealworm *Alphitobius diaperinus*, as well as the house cricket *Acheta domesticus*. Preferably nematode-infected hard-bodied arthropod arthropods are used in accordance with the invention would be infected with nematode infective juveniles.

The term "nematode" refers to organisms of the phylum Nematoda. Examples of nematodes include but are not limited to *Steinernema* or *Heterorhabditis* species. It is contemplated that any and all nematodes species that can utilize an arthropod as a vector and having utility of controlling a pest population could be embodied in the invention as described herein. For instance, the nematode *Heterorhabditis bacteriophora* is used to control pests such as the black vine weevil, *Diaprepes* root weevil, and white grubs.

Nematodes, Insects, and Formulation of Arthropods

*Tenebrio molitor* ($9^{th}$ to $10^{th}$ instar weighing 70 to 90 mg each) were supplied by Southeastern Insectaries, Inc. (Perry, Ga.), *Diaprepes abbreviatus* larvae (40 to 60 days old) were obtained from the Florida Department of Plant Industries (Gainesville, Fla.), and *A. tumida* were provided by J. D. Ellis (University of Florida, Gainesville). Prior to infecting the selected arthropods, the nematodes *H. indica* (Hom 1 strain) and *S. carpocapsae* (All strain) were cultured in *G. mellonella* (obtained from Webster's Waxie Ranch, Webster, Wis.) according to Kaya and Stock (1997). For all experiments, *H. indica* and *S. carpocapsae* infected arthropods were produced on filter paper (Whatman No. 1) based on procedures described by Shapiro-Ilan et al. (2003); insects were inoculated with 200 IJs per insect for *S. carpocapsae*, and 800 (yield experiments) or 600 (efficacy experiments) IJs per insect for *H. indica*. All nematode and insect culturing was conducted at approximately 25° C.

Infected arthropods were formulated using a mechanized tape-packaging apparatus of FIG. 1. FIG. 1 shows the apparatus 10 having a support frame 15 with legs 12. As shown in FIG. 1, the support frame supports a planar board 24. The planar board provides support to the arthropod receptacle 17. In an embodiment of the invention, the receptacle is attached to a vibrator 16 that agitates the arthropods in the receptacle. In another embodiment, the receptacle is continuously rotated to agitate the contents in the receptacle. It is desirable to agitate the contents in the receptacle so that the contents can be picked up by the vacuum tip 19.

In the embodiment shown in FIG. 1, a gantry 26 is supported by the support frame. At one end of the gantry, the vacuum tip 19 sucks up at least one arthropod from the arthropod receptacle 17. The control of the gantry arm and suction through the vacuum tip is controlled by a programmable logic controller 20.

Figure 2:
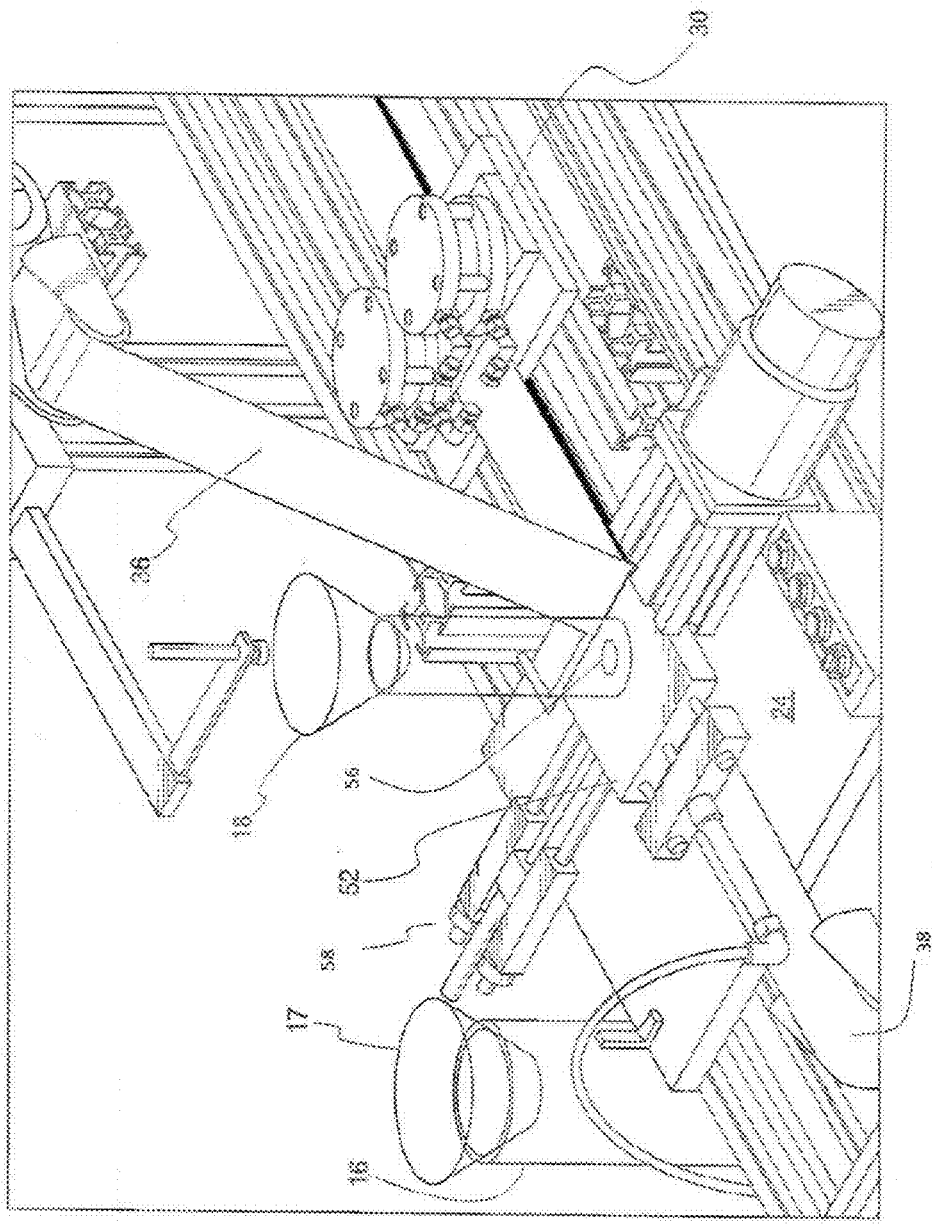
Figure 3:
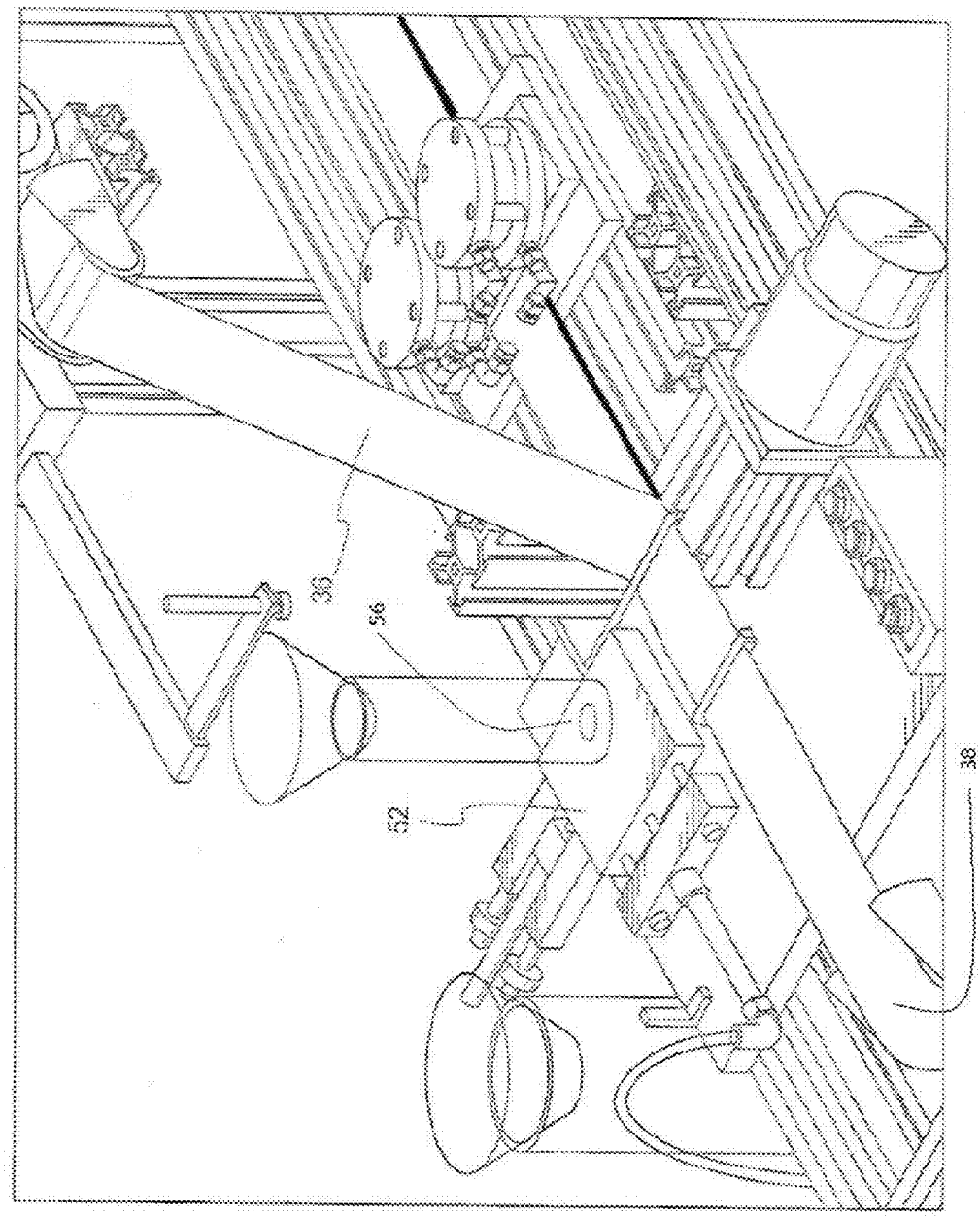
Figure 4:
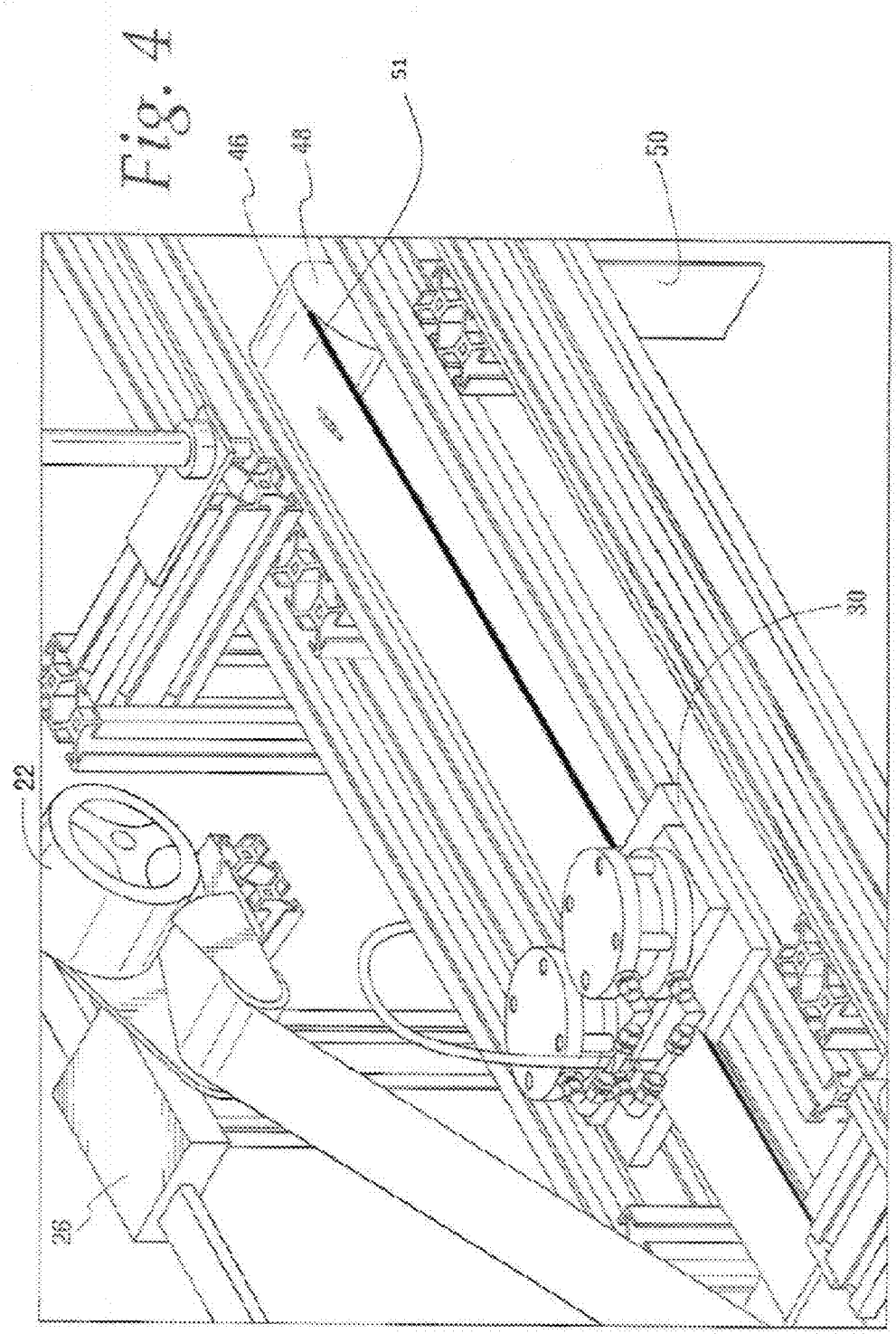
Figure 5:
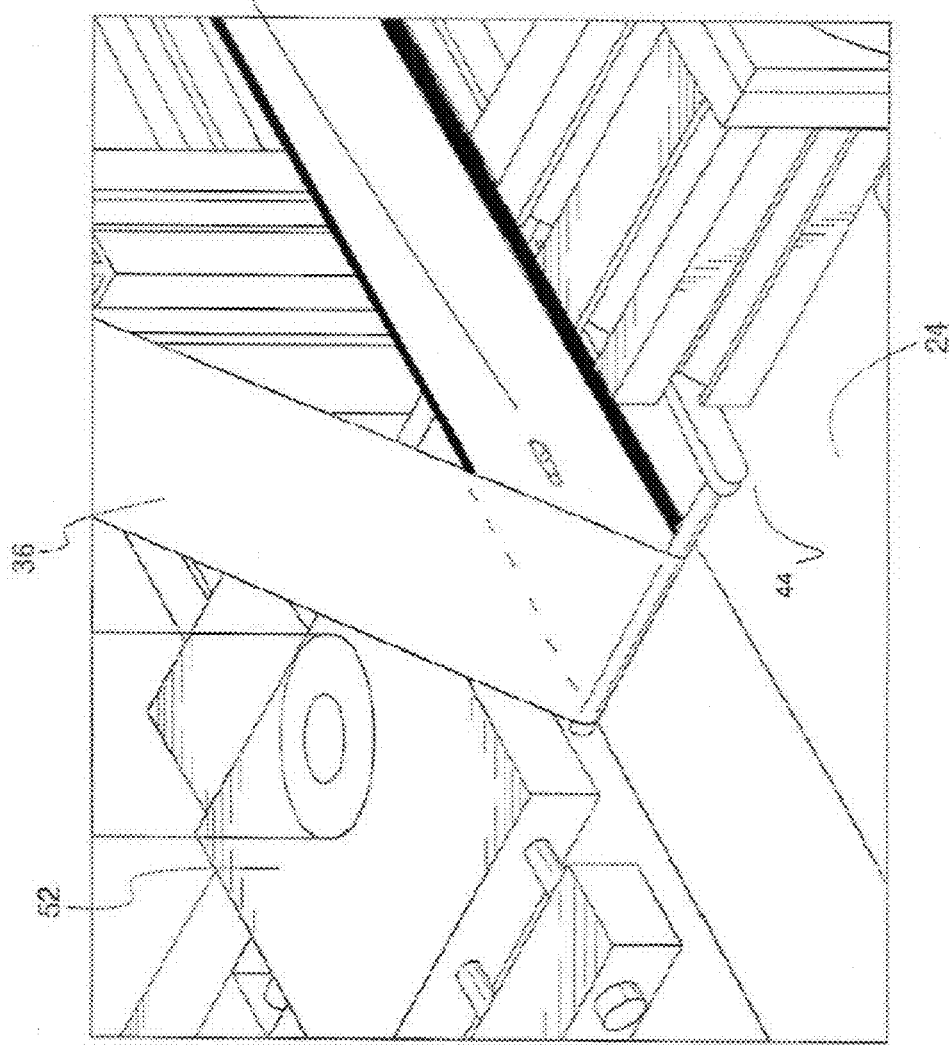

The vacuum tip holding at least one arthropod is programmed to release said arthropod to drop plate 52 on an arthropod positioning module 58. The module can have a receiving cone 18 positioned on the module so arthropods released from the vacuum tip 19 reaches an aperture 56 on the drop plate. The module 58 operable extends and retracts and attached drop plate 52 with the drop plate having at least one aperture 56 allowing for received arthropods released from the vacuum tip. As illustrated in FIG. 3, the arthropod positioning drop plate 52 can be positioned in a retractable position. In the retractable position, the aperture is in a position that arthropods falling through the aperture would not positioned on the first tape 38. As illustrated in FIG. 2, when the arthropod module 52 is in an extended position, the aperture 56 is positioned over a section of the first tape 38. Upon dispensing an arthropod through the aperture 56 on to a section of the first tape 38, the drop plate 52 is retracted to allow a second tape 36 to flank and adhere to the dispensed arthropod between sections of the first and second tape.

As disclosed in FIG. 2, a rotary stationary arm 44 is positioned to apply pressure to adhere a section of the first tape 38 with second tape 36 having an arthropod flanking between sections of the first tape 38 and second tape 36. The rotary stationary arm 44 acts to advance the second tape 36 to package at least one arthropod 51 between sections of the first 38 and second 36 tape.

In one embodiment of the invention, the first tape 38 is dispensed from a first tape head dispenser 32. The first tape dispenser can optionally have a tension knob for adjusting the tension of the first tape 34. The first tape 38 is positioned so that at least one side of the tape adheres to an arthropod that is dispensed through the aperture 56. The second tape 36 is dispensed from a second tape head dispenser 22. The second tape dispenser can optionally have a tension knob for adjusting the tension of the second tape.

In an alternative embodiment of the invention, instead of having tape load on both tape heads 22, 32, only one of the tape heads is loaded with tape. In such this embodiment, the other tape head would be spooled with a backing material conducive to being taped upon. Optimally, the backing material confers rigidity so that arthropods can be flanked between the sections of the backing material and tape in conjunction with the packaging apparatus 10.

In another embodiment of the invention, a rodless cylinder 28 provides support for a tape clamp 30. The tape clamp 30 is programmed to clamp on section tapes not having arthropods flanked between the two pieces. Additionally, the tape clamp 30 traverses linearly on the rodless cylinder while having the clamp engaged to advance the adhered pieces of tape 50.

In an additional embodiment, a vertical stripper cylinder 48 provides rolls adhere tape into a roll. In an alternative embodiment, a rigid guide 46 provides support so that adhered pieces of tapes do not become entangled.

Infected arthropods were formulated using a mechanized tape-packaging machine described in FIGS. 1-5. In the packaging machine, the arthropods are placed in a holding container that is slightly agitated. Individual arthropods are then picked up via vacuum suction and placed at the juncture between extended pieces of masking tape that are automatically dispensed. The tape strips are then clamped together enclosing the arthropod and the joined tapes are advanced at a predetermined interval. Subsequent arthropods are placed at evenly spaced intervals between the tapes. The finished tape strips with arthropods are then formed into a roll for packaging, storage, or direct use. The arthropods in a roll can then be cut out into single or multiple units as needed. A Programmable Logic Controller 20 enables the apparatus to be completely automatic and seal arthropods between two pieces of tape.

Figure 11:
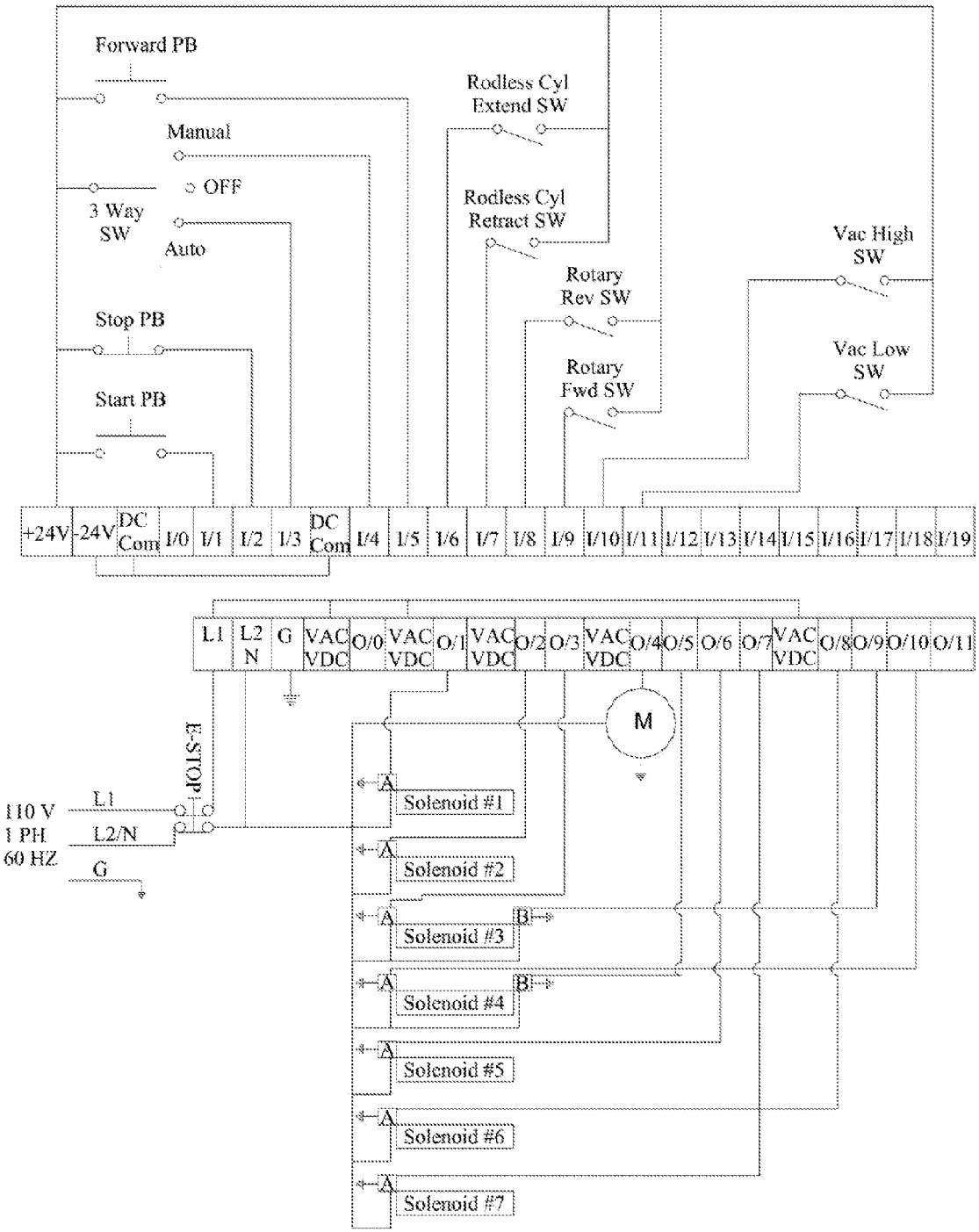
Figure 12:
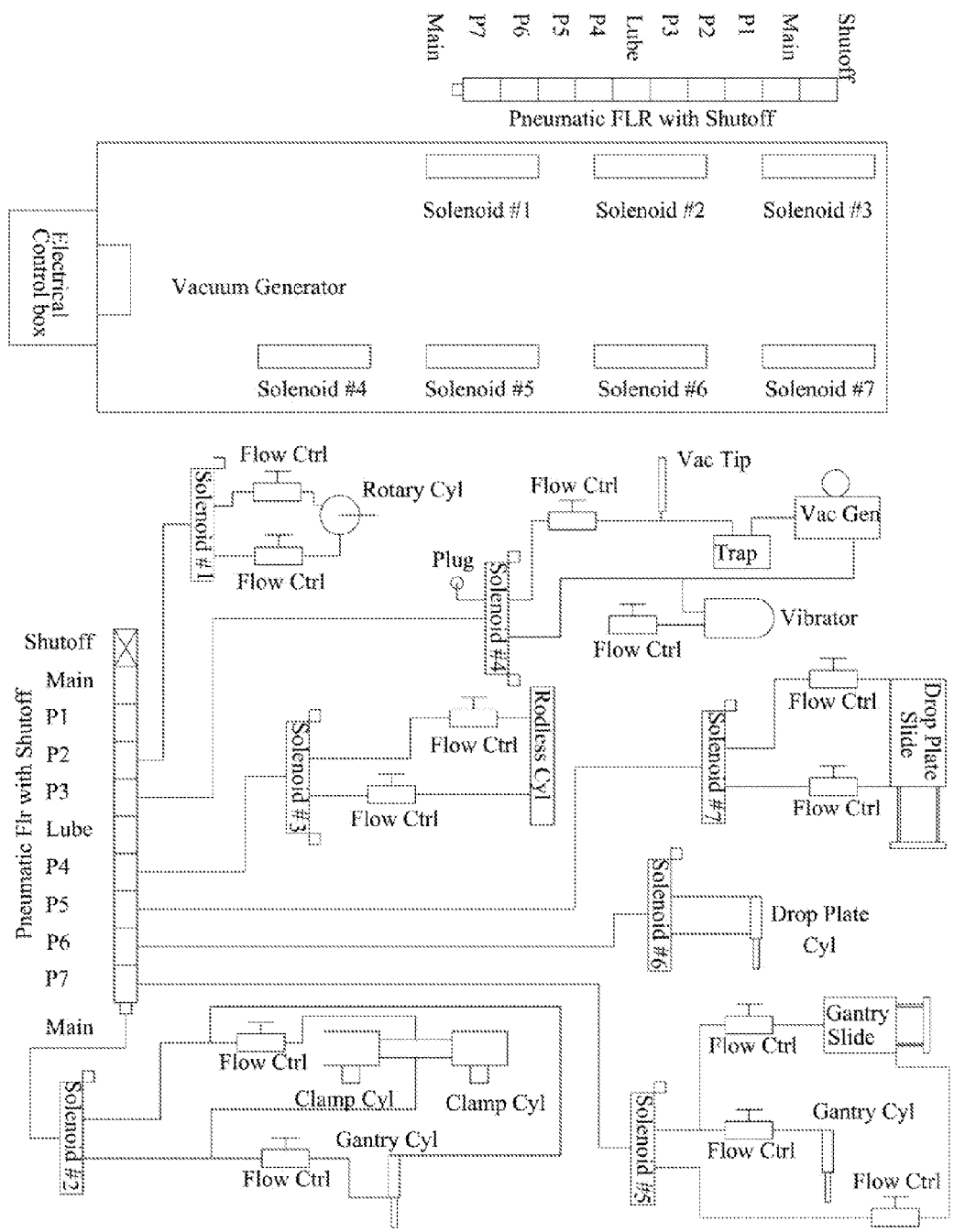

As illustrated in FIGS. 11 and 12, a wiring diagram for the packaging apparatus and a pneumatic diagram is displayed for one embodiment of the invention. In this embodiment, a selection panel switch 42 is in electrically connected with a rotary cylinder 25 that is attached to the rotary stationary arm 44, a vacuum generator 11, drop plate slide 52, and a gantry cylinder.

The following examples are intended only to further illustrate the invention and are not intended to limit the scope of the invention which is defined by the claims. *Tenebrio molitor Aethina tumida, Diaprepes abbreviatus* arthropods are used as model a host, while infective juveniles of *Heterorhabditis indica* and *Steinernema carpocapsae* are used as a model nematode for examples listed below. Differences in percentage of arthropods rupturing, percentage survival of target insects in the pest control efficacy examples, and infective juvenile yields were detected through ANOVA; the Student-Newman-Keuls' test was used to elucidate treatment effects when a significant F value ($P \leq 0.05$) was detected (SAS, 2001). Data from 10 day and 15 day assessments were analyzed separately. Percentage data were arcsine transformed and numerical data (nematode yield) were square-root transformed prior to analysis (Southwood, 1978; Steel and Torrie, 1980, SAS, 2001). In all examples with multiple trials, interactions between trial and treatment effects were not significant ($P > 0.05$); thus, data from trials repeated in time were combined and variation among trials was accounted for as a block effect.

Example 1

Protection of Tape Packaged Arthropods from Mechanical Damage and Nematode Yield Using manual shake tests, the goal was to simulate potential mechanical agitation during shipping or application. The tendency to rupture was evaluated in tape-formulated and non-formulated arthropods at four and sevens days post-inoculation. Five formulated or non-formulated arthropods were placed in a 90 mm Petri dish. The two Petri dishes (one from each treatment) were stacked on top of each other in random order and shaken vigorously for 20 seconds; the arthropods from each nematode species and time of formulation were treated separately. The arthropods in each petri dish were then examined and the percentage ruptured was recorded. To determine yield, after the shaking was complete, arthropods from each Petri dish were placed on White traps and the numbers of infective juveniles emerged was determined after 21 days post-inoculation. Additionally, for inclusion in the yield comparisons, an equivalent set of *T. molitor* were inoculated but not shaken. There were four replicates (Petri dishes) of each treatment and time of formulation and all experiments were repeated once in time (two trials).

TABLE 1

Yield (±SE) of infective juvenile *Heterorhabditis indica* (Hi) or *Steinernema carpocapsae* (Sc) from *Tenebrio molitor* infected hosts with and without tape coverings, and associated statistics.

| Experiment | Treatment | Yield | F | df | P |
|---|---|---|---|---|---|
| *Heterorhabditis indica* - 7 day shake test | Not Taped-Not Shaken | 45,961 ± 8911A | 2.31 | 3, 25 | 0.1004 |
| | Not Taped-Shaken | 40,419 ± 9654A | | | |
| | Taped-Shaken | 42,104 ± 5855A | | | |
| | Taped-Not Shaken | 31,024 ± 8616A | | | |
| *Steinernema carpocapsae* 7 day shake test | Not Taped-Not Shaken | 33,938 ± 7844A | 0.44 | 3, 27 | 0.7270 |
| | Not Taped-Shaken | 28,896 ± 8307A | | | |
| | Taped-Shaken | 30,176 ± 6386A | | | |
| | Taped-Not Shaken | 28,654 ± 7644A | | | |
| *Heterorhabditis indica* 4 day shake test | Not Taped-Not Shaken | 46,295 ± 5080A | 1.17 | 3, 26 | 0.7270 |
| | Not Taped-Shaken | 43,126 ± 5978A | | | |
| | Taped-Shaken | 31,539 ± 4129A | | | |
| | Taped-Not Shaken | 39,373 ± 5519A | | | |
| *Steinernema carpocapsae* 4 day shake test | Not Taped-Not Shaken | 7,438 ± 2083B | 8.37 | 3, 27 | 0.0004 |
| | Not Taped-Shaken | 21,888 ± 5418A | | | |
| | Taped-Shaken | 4,403 ± 971B | | | |
| | Taped-Not Shaken | 4,036 ± 1453B | | | |
| Hi-*Diaprepes abbreviatus* (greenhouse) | Tape | 58,000 ± 8,083A | 0.17 | 1, 6 | 0.70 |
| | No tape | 63,750 ± 11,564A | | | |

$^b$7 d = 7 days post-inoculation; 4 d = 4 days post inoculation (*D. abbreviatus* tests used 7 d arthropods).

Different letters following nematode yields indicate statistically significant differences within each experiment (SNK test, $\alpha = 0.05$).

Figure 6:
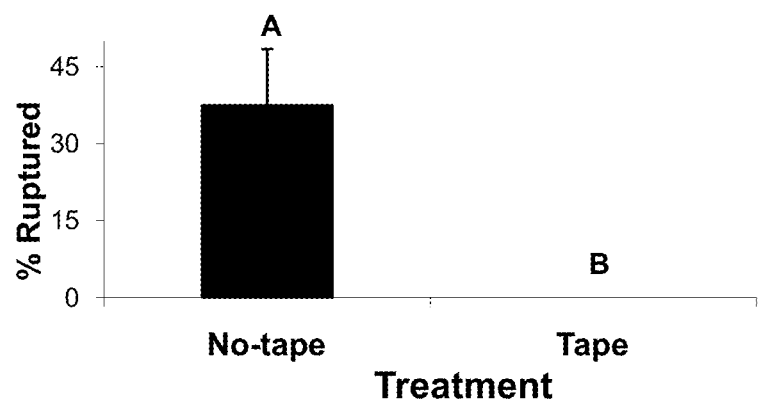
Figure 7:
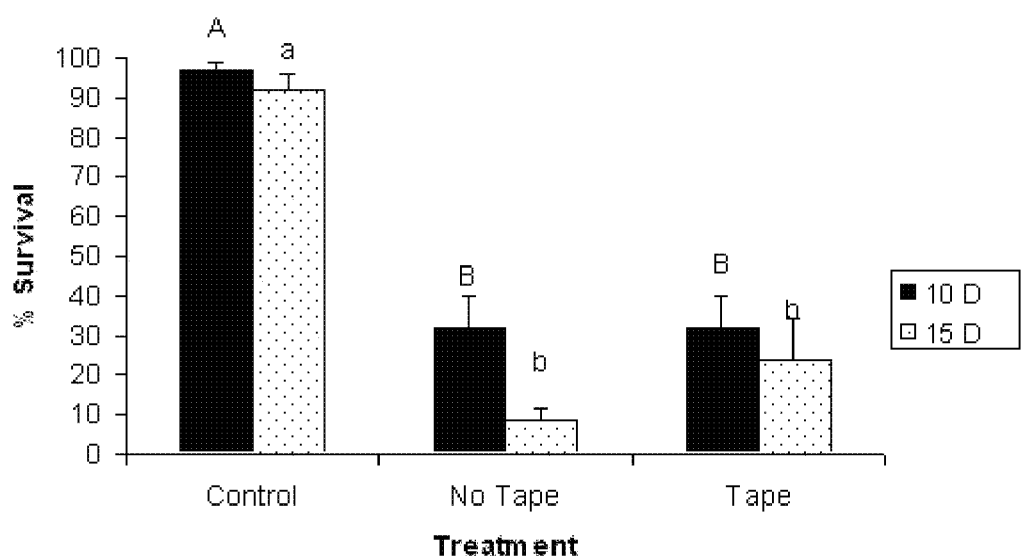
Figure 8:
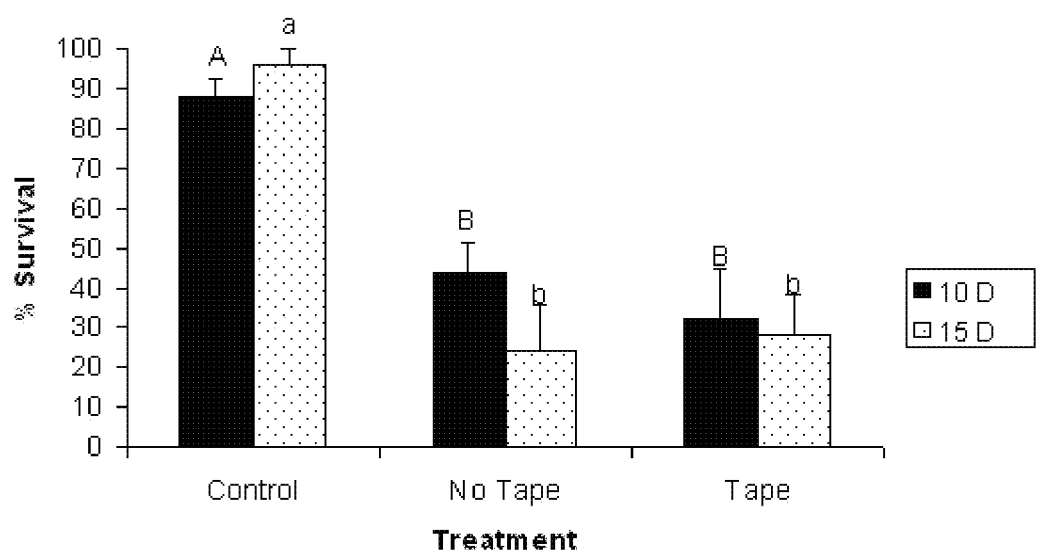
Figure 9:
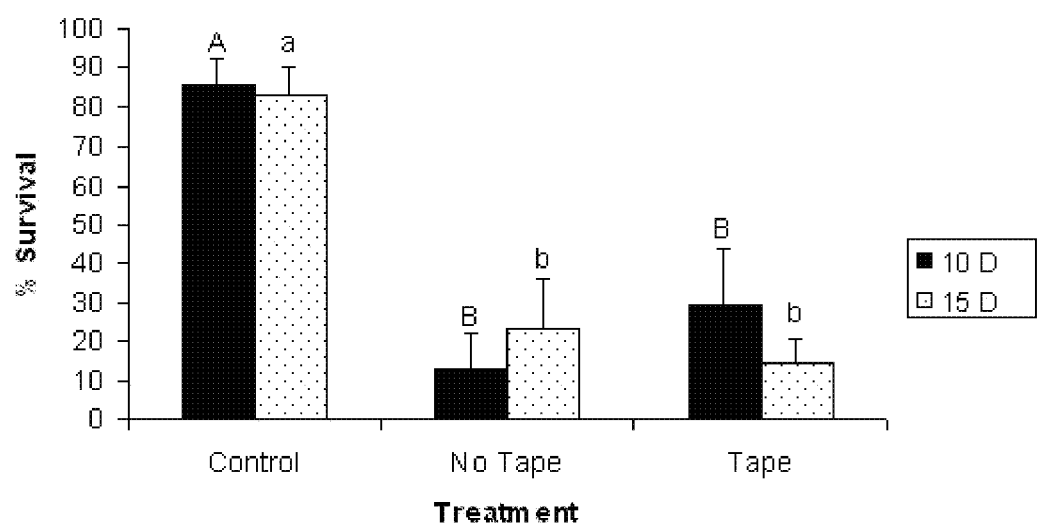
Figure 10:
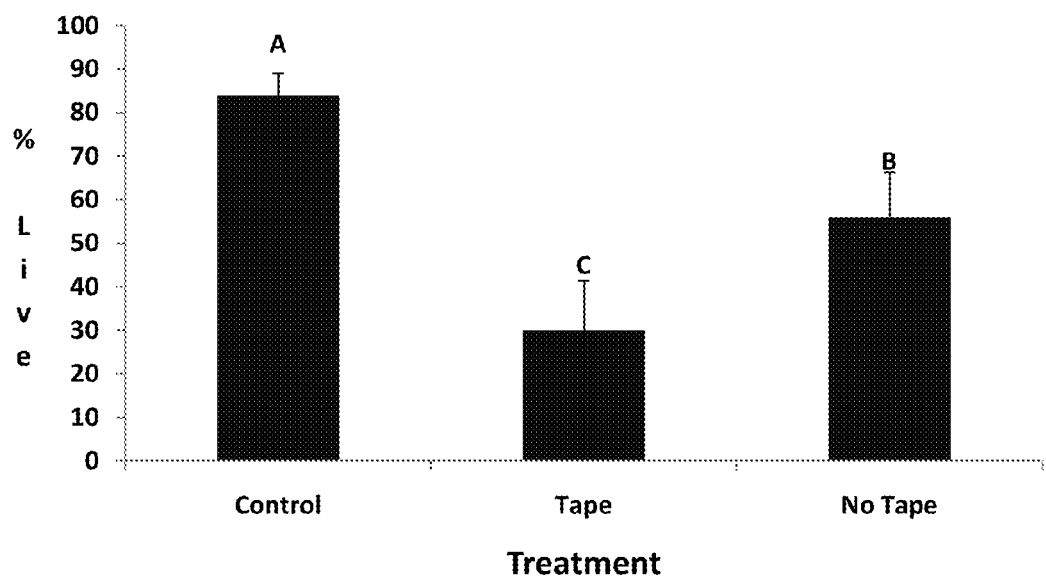

Following mechanical agitation, tape formulated *S. carpocapsae* arthropods were more resistant to rupture than arthropods without tape at 7-d-post infection (F=16.38; df=1, 13; P<0.0014) (FIG. 6). However, no rupturing was detected in any *H. indica* arthropods 7-d-post infection, nor was rupturing detected in arthropods infected with either nematode species 4-d-post-infection.

No differences in infective juvenile yield per insect were detected in arthropods formulated in tape and non-formulated arthropods, except in one instance (*S. carpocapsae* 4-d-post infection) the no-tape treatment that was shaken yielded more infective juveniles than the other treatments including the no-shake/no-tape control (Table 1). The yield of infective juveniles varied among the experiments from 31,024 to 63,750 in *H. indica* and 4,036 to 33,938 in *S. carpocapsae* (Table 1). Also, estimated yields of infective juveniles from arthropods inoculated for use in other experiments (not statistically compared) varied and were (mean±SD) 29,965±10, 231 and 66, 308±25,890 in the first laboratory and second *D. abbreviatus* laboratory trials, respectively.

Example 2

Control Efficacy of Diaprepes Abbreviates with Tape Formulation in Laboratory Potted Soil Conditions In the foregoing examples, the tape formulation had *Tenebrio molitor* infected with the nematodes of *Heterorhabditis indica* or *Steinernema carpocapsae*. For the examples discussed infra, the tape formulation had two infected *Tenebrio*

*molitor* one a piece of tape, approximately one inch in length and packed with the apparatus disclosed herein.

The effects of tape formulated and non-formulated arthropods on survival of *Diaprepes abbreviatus* were evaluated based on procedures described by Shapiro-Ilan, D. I., Lewis, E. E., Tedders, W. L., Son, Y., 2003, "Superior efficacy observed in entomopathogenic nematodes applied in infected-host arthropods compared with application in aqueous suspension" J. Invertebr. Pathol. 83, 270-272, and incorporated herein by reference. Experimental arenas consisted of 13 cm square pots (18 cm depth) filled with potting soil (Metro-Mix 360, Sun Gro, Inc. Bellevue, Wash. USA) and with metal screens on bottom to prevent insect escape. Five *Diaprepes abbreviatus* larvae were introduced approximately 2 cm below the soil surface along with a piece of carrot (ca. 1 cm diam×3 cm long) as food source, which was placed vertically directly below the insect. One day after adding the *D. abbreviatus* larvae, one third of the pots received two *H. indica* infected arthropods with the tape covering, one third received two arthropods without tape, and the last third was left as an untreated control. Arthropods of *T. molitor*, which had been exposed to *H. indica* seven days earlier, were each inserted into test pots approximately 1 cm below the soil surface. At 10 day post-treatment, half of the pots were dismantled and the number of surviving larvae was determined for each pot; the second half of the pots was evaluated at 15 days post treatment. There were five replicate pots for each treatment and control and for each sampling date (30 pots total). The experiment was conducted in the laboratory and repeated once in time with a fresh batch of arthropods (2 trials). A single trial (30 pots) was also conducted in the greenhouse. Temperatures were monitored during the experiments and ranged from 22.8° C. to 25.6° C. in the first laboratory trial, 21.1° C. to 22.2° C. in the second laboratory trial, and 22.7° C. to 30.6° C. in the greenhouse trial.

Data indicated tape formulated arthropods are efficacious in reducing insect pest survival at a level similar to that of non-formulated arthropods. In the laboratory evaluation of *D. abbreviatus*, both the formulated and non-formulated infected *T. molitor* arthropod applications resulted in lower insect survival than the control at 10 d and 15 d post-application ($F=29.32$; $df=2, 32$; $P<0.0001$ and $F=37.95$; $df=2, 32$; $P<0.0001$, for the 10 d and 15 d assessment dates, respectively), and there were no differences detected between the two treatments (FIG. 7). If Abbott's formula (Abbott, 1925) is applied to the *D. abbreviatus* survival data in the laboratory, the level of control at 15 days post-application was 75.0% and 90.9% in the tape and no-tape treatments, respectively. Similar to the laboratory trials, in the greenhouse test, no differences in *D. abbreviatus* survival were detected between the formulated and non-formulated arthropods at 10 days and 15 days post-application, and both treatments caused lower *D. abbreviatus* survival than the control ($F=8.94$; $df=2, 12$; $P=0.004$, and $F=16.92$; $df=2, 12$; $P=0.0003$ for the 10 days and 15 days assessment dates, respectively) (FIG. 8). Based on Abbott's formula, the level of control at 15 days post-application was 70.8% and 75.0% in the tape and no-tape treatments, respectively.

Example 3

Control Efficacy of *Aethina Tumida* with Tape Formulated in Laboratory Potted Soil Conditions The effects of the tape-formulated versus non-formulated arthropods on the survival of *A. tumida* was conducted in the laboratory in a similar manner to the *D. abbreviatus* in Example 2. evaluation except that the arenas consisted of plastic containers (11 cm top diam., 8 cm bottom diam., 8 cm depth, with approximate 0.5 mm holes on bottom) containing 10 last instar *A. tumida* each, and the arenas did not contain carrots. The containers were lidded during the experiment to prevent insect escape. Each trial contained four replicate containers for each treatment and each assessment date (10 and 15 days) resulting in 24 containers total. All other parameters were the same as those described for the *D. abbreviatus* evaluation. The experiment was repeated once in time (two trials); the first trial was conducted simultaneously with the first *D. abbreviatus* laboratory trial (using the same batch of *T. molitor* arthropods), whereas the second trial was conducted separately. Temperature was monitored during the experiment and ranged from 22.8° C. to 25.6° C. in the first laboratory trial, and 21.1° C. to 22.2° C. in the second trial.

The pest control efficacy results in the *A. tumida* experiment were similar in that the *D. abbreviatus* experiments in Example 2 in that the infected arthropod applications resulted in lower insect survival than the control at 10 days and 15 days post-application, and there were no differences detected between the tape and no-tape treatments ($F=15.03$; $df=2, 23$; $P<0.0001$, and $F=24.55$; $df=2, 23$; $P<0.0001$, for the 10 days and 15 days assessment dates, respectively) (FIG. 9). Based on Abbott's formula, the level of control at 15 days post-application was 78.0% and 67.8% in the tape and no-tape treatments, respectively.

Example 4

Control Efficacy of *Aethina Tumida* with Tape Formulation in Field Conditions To evaluate the tape-formulated in field conditions, conditions were setup in as described in Example 3. The treatments included mealworm (*Tenebrio molitor*) cadavers infected with *Heterorhabditis indica* nematodes and formulated in tape, a treatment of infected mealworm cadavers without any tape formulation, and an untreated water control. The experimental units consisted of one pint plastic containers with screened bottoms to allow drainage. The containers were filled with field soil and buried in the ground so that the soil in the container was level with the natural soil in a vegetable field in Perry, Ga. The rate of application was two infected cadavers per pot. Ten larvae of the small hive beetle (*Aethina tumida*) were placed in each container and allowed to burrow down into the soil. There were five replicate containers for each treatment. Survival of insect larvae was determined ten days post-treatment.

Results indicated in FIG. 10 showed that both nematode cadaver treatments (with and without tape) caused statistically significant suppression of small hive beetle survival ($P<0.05$) compared with the control. Additionally, the cadaver treatment with the tape formulation caused greater suppression than the cadaver treatment without tape ($P<0.05$; FIG. 10).

While the invention has been described with reference to details of the illustrated embodiment, these details are not intended to limit the scope of the invention as defined in the appended claims.

The embodiment of the invention in which exclusive property or privilege is claimed is defined as follows:

1. A taping apparatus for packaging arthropods, the apparatus comprising:

a receptacle for holding arthropods having been infected with entomopathogenic nematodes, a first tension adjustable tape head for dispensing a first tape, a transferring means for transferring at least one arthropod from the receptacle to a position on said first tape with the arthropod adhering to the first tape, a second tension adjustable tape head for dispensing a second tape with said second tape positioned to adhere to a section of said first tape upon said first tape receiving said arthropod with the second tape adhering to the arthropod and first tape, a rotating stationary arm that applies pressure to said second tape with said first tape section having an arthropod positioned thereupon; and a means for translocating a section of tape with first and second tape adhered together along a linear path to allow said first tape to receive a subsequent arthropod from said transferring means, wherein the adhered tape form a continuous line of packaged arthropods.

2. The apparatus of claim 1 further comprising a power source configured to provide electric current to the taping apparatus; and a programmable control unit configured to control the taping apparatus unit and/or the power source.

3. The apparatus of claim 1 wherein the transferring means is a vacuuming means that provides vacuum pickup of an arthropod from the receptacle and dispenses said arthropod to an aperture on drop plate, with said drop plate being positionable to deposit a dispensed arthropod from the aperture to a section on the first tape.

4. The apparatus of claim 3 further comprising an agitator that agitates arthropods held in the receptacle.

5. The apparatus of claim 1 wherein the translocation means is a tape clamp positioned to clamp on to a portion of adhered first and second sections of tape not having any arthropods in between said portions with the clamp traversing a rodless cylinder to allow subsequent transferring of arthropods to a section on the first tape.

* * * * *